United States Patent [19]

Brar et al.

[11] Patent Number: 4,654,465

[45] Date of Patent: Mar. 31, 1987

[54] GENIC MALE-STERILE MAIZE

[75] Inventors: Gurdip S. Brar, Middleton; Oliver Nelson, Cross Plains, both of Wis.

[73] Assignee: Agracetus, Middleton, Wis.

[21] Appl. No.: 756,746

[22] Filed: Jul. 18, 1985

[51] Int. Cl.$^4$ .............................................. A01H 1/02
[52] U.S. Cl. ........................................ 800/1; 47/58; 47/DIG. 1
[58] Field of Search .................... 47/58, DIG. 1, 1; 800/1

[56] References Cited

U.S. PATENT DOCUMENTS 3,710,511  1/1973  Patterson ............................... 47/58

Primary Examiner—Robert E. Bagwill
Attorney, Agent, or Firm—Nicholas J. Seay; Albert P. Halluin

[57] ABSTRACT

A method is disclosed for creating and utilizing genic male-sterile maize for hybrid maize production. The method makes use of the Spm transposable element system and involves creation of a mutated male fertile allele, mutated by the presence of the Spm suppression receptor therein, expression of which is suppressed in the presence of the Spm suppressor. Methods are disclosed for transferring this system into any inbred line of interest for use in hybrid seed production.

20 Claims, No Drawings

GENIC MALE-STERILE MAIZE

FIELD OF THE INVENTION

The present invention relates generally to genetic procedures involving maize plants and relates more particularly, to procedures intended to develop and utilize male-sterile maize seed for use in hybrid maize production.

BACKGROUND OF THE INVENTION

In current maize, or corn, production in the United States, the vast majority of the seed maize utilized by commercial farmers are singlecross, F1 hybrid varieties. The current commercial techniques for producing hybrid maize seed require that predictable cross-breedings be achieved between specifically selected male and female parent plants. Thus plants of the designated male and female lines are planted together in a common field so that pollen from the male parent plants can travel and pollinate the female parent plants.

This procedure is facilitated by the hermaphroditic character of maize plants. Each plant has separate male and female inflorescences. Thus, in order to ensure that a proper cross is made between the desired male parent plant and the desired female parent plant, it is necessary to ensure that pollen from the female parent plant does not self-pollinate that same plant or pollinate a sibling female parent plant. In order to ensure that such undesirable self-pollination or sibling pollination does not occur, the common practice in the industry is to remove physically the male infloresena from the designated female parent plants by detasselling the female parent plants by hand. While mechanical devices are presently available in the art to detassel the female parent plants, because of the variability in size of maize plants in any given field and the necessity for not cutting too much of the maize plant away, mechanical processing is not efficient, and thus the detasselling procedure is conventionally done by hand, sometimes in combination with a mechanical device. This process is a very labor-intensive activity and is concentrated in its time period, normally a time period of four to six weeks in June, July or August, in the northern hemisphere, because the activity must be performed at closely spaced intervals during the flowering period of the maize inbred used as a female parent. This detasselling operation is both a difficult logistical operation, because of the need to acquire large amounts of short-term labor, and is an expensive process because of its labor intensiveness.

Accordingly, much effort has been spent over time to develop maize plants which are male-sterile. The term male-sterile generally designates a plant wherein the male inflorescences organs on the mature plant produce no viable pollen, but the plant still has complete female reproductive capability. The use of male-sterile maize plants in a hybrid production system avoids the need for detasselling, since the only pollen available for the designated female parent plants, which are male-sterile, is the pollen produced by the designated male parent plant. In this way predictable crosses can be made so that hybrid progeny suitable for field use can be created. Unfortunately, the use of male sterile maize plants has previously had several inherent disadvantages.

There are two categories of presently known and used systems for maintaining male-sterile stocks of maize plants. One system relies on a so-called cytoplasmic, or non-nuclear, male-sterile trait, and the other system relies on genic, or nuclear, trait inheritance to maintain male sterility.

The cytoplasmic male sterility system relies on genes not contained in the nucleus of cells, hence the name. This system is more properly termed cytoplasmic-nuclear since it depends on both a cytoplasmic gene and the absence of a nuclear restorer genes for male sterility. Since cytoplasmic genetic material is normally transmitted solely from the female parent plant in maize, and is only very rarely, if ever, passed through pollen, the use of a cytoplasmic male-sterile trait in a female parent line allows pollen to be donated by a male-fertile parent while the resulting progeny plants are reliably male-sterile because of the cytoplasmic gene contribution of the female parent. One system disclosed for use of cytoplasmic male sterility to produce commercial hybrid maize is disclosed in U.S. Pat. No. 2,753,663.

For a time the United States hybrid seed industry utilized cytoplasmic male sterile maize lines for the production of hybrid maize seed. The most popular type of cytoplasmic male sterility was referred to as the Texas-Sterile or T-Sterile cytoplasm. This cytoplasmic sterility was used widely in producing several types and varieties of hybrid seeds for sale until 1970 when an epiphytotic of a race of T-type *Helminthosporium maydis* occurred causing a form of southern leaf blight in most of the then existing male-sterile plants and hybrids produced from them. This event convinced many maize breeders that cytoplasmic male sterility was an inherently inappropriate mechanism for achieving male-sterile plants since the differences between normal cytoplasm and that carrying male sterility seems inherently to affect not only pollen fertility but also disease susceptability as well. In addition, the heavy damage caused by this epiphytotic event has created a widespread reluctance to use cytoplasmic male-sterile lines because of consumer fears about reoccurrence of an epiphytotic in other cytoplasmic male-sterile lines. To date, two other cytoplasmic male sterility lines have been identified. Referred to as the C and S types, these types have inherent problems of stability and sterilization of inbred lines in addition to the normal consumer and breeder reluctance to use a cytoplasmic male-sterile system.

The other basis for male-sterility in maize plants is genic male sterility in which the nuclear genes of the maize plant cause male-sterility. Much work has been done on identification of male-sterile genes in maize, and, to date, at least nineteen different nuclear gene mutations are known which can produce male sterility. See the list of male-sterile genes, for example, in Column 15 of U.S. Pat. No. 3,861,079. In every presently known heritable trait which produces male sterility, the sterility is determined by a single gene, and the allele for male sterility is recessive. The possibility of using genic male-sterile lines has long been available to producers of hybrid seed but has not proved very practical to use.

The problem with the use of conventional genic male sterile lines is that it is inherently impossible to maintain an inbred stock which is homozygous for the recessive allele giving rise to male-sterility. The reason for this is simply that plants of the line are incapable of producing the pollen necessary to self-pollinate or pollinate siblings homozygous for the recessive allele. It is, of course, possible to cross-pollinate male sterile plants homozygous for the male-sterile recessive allele with male-fertile plants which are heterozygous for the male-sterile gene, i.e. having in their genic pair one male-fertile allele and one male-sterile allele (Ms/ms). The progeny from this cross-breeding would be approximatey 50% male-sterile and approximately 50% male-fertile. Thus if it was intended to use plants from a simple genic male-sterile line as female parents in a cross-fertilization scheme, the best that could be expected is that 50% of the progeny plants intended for use in hybrid seed production would be male-sterile. Therefore a detasselling operation would be necessary, in any event, to detassel the other 50% of the plants. Since detasselling is thus necessary anyway in a field utilizing this procedure, there is little commercial advantage to using this process, and it is not widely used at present.

One other approach to create genic male-sterile plants for use in hybrid seed production has been documented. A technique developed by Patterson utilizes reciprocal translocations and various forms of chromosome deficiencies and duplications to produce male sterile stocks. This procedure is described in detail in the disclosures of U.S. Pat. Nos. 3,710,511 and 3,861,079. That procedure need not be described in detail herein except to suggest that the approach that it uses to create genic male-sterile plants differs completely from the approach suggested herein, although the objective of both approaches is to produce genic, as opposed to cytoplasmic, male-sterile plants for hybrid seed production.

The system of the present invention makes use of one example of a class of genetic elements known as transposable elements. Transposable elements are genetic elements which can spontaneously relocate themselves from one locus to another on a chromosome or to anywhere on any other chromosome located in the plant genome. Transposable elements were first identified in maize, in the pioneering work of Dr. Barbara McClintock. Several systems of transposable elements have been identified by Dr. McClintock initially, and others subsequently. Transposable elements have now been identified in other species, including bacteria and animals, but are best characterized in maize.

Among the systems of transposable elements identified by McClintock, the system of particular interest to us is the Suppressor-mutator (Spm) system (McClintock, 1955). The same system was independently isolated by Peterson (1953) who referred to the components as Enhancer (En) and Inhibitor (I). Spm is a transposition-competent (autonomous) element which encodes the information enabling its excision from one location in the genome and reintegration at another location. It affects the expression of any locus in which it inserts. A second component may also be present, constituting a two element system. This second component has been shown to be a defective Spm in which a portion of the DNA sequence of Spm has been deleted (Pereira et al., 1985) and which has concomitantly lost the ability to catalyze its own transposition, but it can be induced to transpose when an Spm is present in the genome. This transpositiondefective derivative of Spm has been variously referred to as the receptor of Spm, Rs, and I. We will refer to this second component as a defective Spm (dSpm), since its origin is now understood in molecular terms, and also as a receptor factor (Rs), which defines its functional role.

These defective Spms can transpose from one locus and reintegrate in a second locus when an active Spm is present in the genome. In the absence of Spm, a dSpm is stably integrated in a locus where it may or may not affect the phenotype of the plant homozygous for that locus (McClintock, 1965). When an Spm is present in the genome, it suppresses all activity of any locus in which a dSpm has inserted thereby producing a mutant (null) phenotype until the dSpm responds to a transacting signal from Spm by being excised from the locus. If this excision event restores the normal organization of the locus in a cell, that cell and its clonal descendants will have a nonmutant (normal or wild type) phenotype. It is the possibility that a dSpm can integrate into a locus in such a manner that a nonmutant phenotype is produced in the absence of an active Spm but in the presence of an active Spm, gene activity is suppressed and a mutant phenotype is produced, that is of particular importance to this process of hybrid seed production. The Spm transposable element system is being used as a switch to turn off gene activity and produce male-sterile plants when desired for the purpose of hybrid seed production.

In this connection, it is desirable although probably not necessary to produce and utilize Spm's that have attenuated or null mutator activity in order to eliminate the possibility that an Spm-catalyzed excision of a dSpm integrated into an Ms allele (and producing a male-sterile phenotype in the presence of an active Spm) can occur sufficiently early in plant development to produce male-fertile sectors in the tassel. Thus, we desire Spm elements which are themselves partially defective having lost mutator activity but retaining Suppressor activity. McClintock has reported such partially defective Spms.

SUMMARY OF THE INVENTION

The present invention is summarized in that maize seed is produced which upon cultivation will yield genetically stable male-sterile maize plants, which seed maize includes, in its genome: a suppression factor capable of activation of a receptor factor elsewhere in the genome; a male-sterile allele; and an insertion mutant male-fertile allele allelic with the male-sterile allele and mutated by the insertion therein of a receptor factor relative to the male-fertile allele so as to allow male-fertility in the absence of the suppression factor and to suppress male fertility in the presence of the suppression factor.

It is also an object of the present invention to provide a method of producing male-sterile maize seed which includes the steps of pollinating maize plants homozygous for male sterility at a selected male-sterile locus and homozygous for a suppression factor elsewhere in its genome with pollen from maize plants homozygous for a mutant male fertile allele at the same selected male-sterile locus, the mutant male fertile allele mutated by the insertion therein of a suppression receptor factor operative to suppress expression of the male fertile allele in the presence of the suppression factor in the genome, and harvesting the seed produced from the homozygous male-sterile plants.

It is an object of the present invention to produce and use in the production of hybrid maize seed production genic male-sterile plants which are stable, reliably sterile, and not inherently susceptible to pathogenic activity.

It is another object of the present invention to produce and use male-sterile plants in a breeding system which can be transferred to any desired inbred maize line.

It is yet another object of the present invention to provide such a system for producing genic male-sterile plants in which the male sterility is closely linked with endosperm color, or other easily recognized seed phenotype, so as to make optical selection of male-sterile seed easily possible.

Other objects, advantages, and features of the present invention will become apparent from the following detailed description and examples provided hereafter.

DESCRIPTION OF THE PREFERRED EMBODIMENT

The system described here is intended to allow plant breeders to make and reliably reproduce genic male-sterile maize by making use of the components of the Spm (Suppressor-mutator) transposable element system in a coordinated procedure in which parent stocks which are reproducible and maintainable can be directly used to create a genic male-sterile progeny generation for hybrid maize production. The two specific parent stocks are required to have specific alleles for a selected male-sterile locus. One of the two parent stocks, as will be disclosed, carries a defective copy of the transposable element system, which functions as a receptor, while the other parent stock carries a copy of the entire suppressor-mutator element, although preferably with an inactive mutator. The system disclosed here includes a methodology for generating the required two parent plant stocks from the same inbred maize line so that the male-sterile plants can be reliably generated from that single inbred maize line and thus that particular maize line or, by extension, any other inbred maize line can be used for hybrid maize production as a female parent with the remainder of its genome remaining intact. Also disclosed here is the procedure used to utilize the parent stocks to create male-sterile plants.

The procedure to produce the required parent stocks for male-sterile maize production begins with the creation of an insertion mutant male-fertile allele. To create this allele it is first necessary to select a transposable element system and a male-sterile locus to be utilized. The transposable element system must include two functional elements which can be separately located in the genome of the plant. One functional element is a receptor factor which is, if inserted properly, capable of preventing the expression of an allele in which it is placed when, and only when, a separate functional suppression factor is located somewhere in the genome of the plant. Each of these functional elements is, in reality, a complete or defective copy of the Spm element, with the receptor factor defective for the suppression function and with both elements preferably having inactive mutators. The defective Spm (dSpm) functioning as the receptor factor must be properly inserted in the male fertile allele to achieve the controllable male-sterility desired.

It is critical, as will be seen in detail later, that the suppression factor be capable of actuating the receptor factor to prevent male-fertile gene expression when the suppression factor is located in the genome. Use of the Spm system to create receptor and suppression factors allows prevention of gene expression when the receptor is properly inserted regardless of where the suppression factor is in the genome. At present, given the limitations of our present knowledge of transposable elements in maize, of the presently known element systems only the Spm system is capable of functioning within the system of the present invention. It is to be understood, however, that other transposable elements may be discovered in maize and that there may indeed be other element systems which have two components capable of functionally serving the purposes of the Spm elements disclosed in accordance with the present invention. Similar systems may also be usable in other crop or horticultural plants. Thus while the invention is described in specific detail with regard to the Spm suppressor-mutator transposable element system in maize, it is to be expected that other similar transposable element systems, if identified later, may also be used within the scope of the present invention in maize as well as in other plants.

It is also necessary at the outset of utilizing this procedure to select a male-sterile locus to be used in the system. At present some nineteen different chromosomal loci of male-sterile genes have been identified. At all the known male-sterile loci recessive alleles condition male sterility and dominant ones condition male fertility. The present invention may make use of any of these loci. The present invention is described here with particular application to the $ms_1$ male-sterile locus. The $ms_1$ locus was selected for use in the system of the present invention because it is tightly linked to a gene controlling endosperm color in maize seed. This tight linkage, which allows only approximately 0.5% recombination, can be utilized in the present system to correlate a recessive male-sterile gene with a specific endosperm color and can be used to conveniently select specifically homozygous male-sterile plants by screening for the proper endosperm color. It is, however to be understood, that other male-sterile loci may also be used within the present invention.

The hybrid maize production scheme disclosed here using the Spm system and endosperm color linkage requires specific parent stocks having specific male-sterile or male-fertile alleles at a common male-sterile locus. These are the required lines:

$$\frac{msy}{msy} \quad \frac{Sp}{Sp} \tag{A}$$

$$\frac{Msy}{msY} \quad \frac{Sp}{Sp} \tag{B}$$

$$\frac{Ms(Rs)\ Y}{Ms(Rs)\ Y} \tag{C}$$

Where Sp refers to an Spm preferably with the lack of an active mutator (and thus functioning only as a suppression factor) and Ms(Rs) refers to a dSpm having an inactive suppression factor (and thus functioning only as a receptor factor) which is inserted in the Ms allele so that gene expression is prevented when an Spm suppression factor is present anywhere in the genome. Lines (A) and (B) are crossed and selected for yellow endosperm color (temporarily ignoring recombinations) to yield a stock $$\frac{msy}{msY} \quad \frac{Sp}{Sp}$$

which is crossed to line (C) to yield equal proportions of the following stocks:

$$\frac{msy}{Ms(Rs)\ Y} \quad \frac{Sp}{—} \quad \text{and} \quad \frac{msY}{Ms(Rs)\ Y} \quad \frac{Sp}{—}.$$

All the seed of this generation is male-sterile and can be used for hybrid seed production by crossing to any desired male parent line. In these plants the Ms(Rs) allele is inactivated by the presence of the Spm suppression factor preventing the male fertile allele from expression.

Recombinations during the cross of lines A and B would lead to some male fertile plants to be rogued out and some (>1%) white kernels in the product.

As an alternative to the above procedure, it would also be possible to cross (A) directly to (C) to yield all $$\frac{msy}{Ms(Rs)\ Y} \quad \frac{Sp}{-}$$

stock which could be used as a female parent in hybrid seed production. This method would result in more white kernels in the feed production stage and thus may be less desirable.

Before hybrid seed production can begin, it is first necessary therefore to generate the parent stocks by detecting transfer of a receptor factor in an Spm-carrying maize line to the male-sterile locus selected. Male-sterile plants are used as a female parent to be crossed by an Spm carrying stock. The F1 generation produced by this cross would normally be expected to be fully male-fertile because each of the plants should be heterozygous for male fertility and male sterility alleles (Ms/ms) at the desired male-sterile locus. However, transpositions caused by the Spm system should cause a small percentage of the F1 plants to be male-sterile, and those F1 plants which are male-sterile may have a full or defective copy of the Spm system located at the male-sterile locus. By screening the F1 plants for male-sterility, one should obtain some plants which carry the desired dSpm, functioning as a receptor factor at the desired male-sterile locus. To test for dSpm insertion at the desired locus, the F1 male-sterile plants can be crossed to a uniform genetic background to obtain the mutated gene at the desired male-sterile locus in uniform background plant stock. Plants of that stock (F1) can then be test crossed with the male-sterile stock (ms$_1$Spm/ms$_1$Spm) and the expected result of the cross can be compared with the actual result to determine if the mutated allele is in fact affected by the Spm system. If the male-sterile allele is the stock resulted from a random male-sterile mutation, then the self cross of the progeny (F1' self cross) and the test cross (F1'×ms$_1$Spm/ms$_1$Spm) will produce progeny which will be expected to be about 25% and 50% male-sterile. However, if the male-sterility is due to the presence of insertion of a dSpm in the male-fertile allele, then the self cross progeny (F1'selfed) will be male-fertile in the absence of Spm and the test cross progeny (F1'×ms$_1$Spm/ms$_1$Spm) will be 50% or 100% male-sterile depending on whether the F1' plant was heterozygous (Ms(Rs)/Ms) or homozygous (Ms(Rs)/Ms(Rs)) for the mutated allele. If another, non-defective copy of the Spm is present in the F1', then the results could vary between these extremes.

Once it is determined that a dSpm copy functioning as a receptor is located at the appropriately selected male-sterile locus, it is then most helpful to attempt to eliminate or partially inactivate the mutator from the all copies of Spm system in the stocks used, and particularly from the breeding stock donating the suppressor function. This can be done separately from the stock line used to generate the mutated male-sterile gene by starting directly with the bronze mutable-13, or other Spm carrying stock line, and by breeding from transposed progeny plants which exhibit repression but which are genetically stable.

At this stage in the procedure there are two important plant lines. One plant line contains a dSpm copy functioning as a receptor, inserted at a desired male-sterile locus, and the other stock line should be homozygous for male sterility at that same locus with an Spm copy functioning as a suppressor (preferably with an inactivated mutator) also located elsewhere in the plant genome. The next step is to transfer both of these components to an appropriate inbred maize line desired for use in hybrid maize production. The inbred line is used as a recurrent parent and the line carrying the receptor at the desired male-sterile locus is used as a nonrecurrent parent. Backcrosses are done against the pure inbred parent line until the mutated male-sterile gene is transferred to the background inbred line. The progeny from the back crosses can be crossed to a tester stock, consisting of the homozygous male-sterile line containing a functional suppressor component, to select for plants which are heterozygous for male fertility and for the mutated male-fertile allele carrying the dSpm receptor function therein.

As stated previously, to use an inbred line in hybrid maize production under the present system, it is necessary to have two parent generation stocks, one with the mutated male-fertile gene and the other with an Spm suppressor function contained in the genome of the plant which is otherwise of the inbred line. Beginning again with the inbred line stock, which is again used as a recurrent parent, a homozygous male-sterile line containing the Spm suppressor in its genome at a location other than the male-sterile locus is used as a non-recurrent parent. A tester stock consisting of male-sterile plants containing the Spm receptor is used to isolate the desired plants which will be homozygous male-sterile containing the suppressor component of the Spm system.

As will be described below, the use of the ms$_1$ locus allows an endosperm color Y1 gene to be utilized as a marker for male sterility in such a manner that selecting for the linked marker will vastly enrich the proportion of the progeny which are male-sterile.

The procedure detailed above is intended to create three source stocks which can be identified as follows:

$$\frac{msy}{msy} \quad \frac{Spm}{Spm} \tag{1}$$

$$\frac{Msy}{msY} \quad \frac{Spm}{Spm} \tag{2}$$

$$\frac{Ms(Rs)\ Y}{Ms(RS)\ Y} \tag{3}$$

Where ms is a recessive allele and conditions male-sterility, Ms is a dominant allele which conditions male fertility, Y is recessive and conditions endosperm color white, Y is dominant and conditions for endosperm color yellow; Spm is the suppressor function of Spm (preferably a full Spm copy with inactive mutator) and Ms(Rs) is a male fertile mutated allele having the Spm receptor function (i.e., a dSpm lacking suppressor function) located in the male fertile gene. These stocks are the ones generated in the procedure as discussed so far. Stocks (1) and (2) are maintained by crossing with maintainer stocks. Stock (1) is maintained by crossing msy/Msy; Spm/Spm which yields equal numbers of the desired homozygous male-sterile plants ($ms_1/ms_1$) and discard heterozygous male-fertile plants ($Ms_1/ms_1$). The stock (2) is maintained by crossing to msY/MsY; Spm/Spm which also yields equal numbers of male-fertile and male-sterile plants with the male-fertile plants being kept.

To use these stocks in practice (1) is first crossed with (2) to yield mostly $$\frac{Msy}{msy} \quad \frac{Sp}{SP} \text{ and } \frac{msy}{msY} \quad \frac{Sp}{Sp}$$

The seeds for male fertile plants can then be screened out and discarded based on white endosperm color. The 1% recombination rate may result in some $$\frac{msy}{msy} \quad \frac{Sp}{Sp}$$

plants being discarded and may also result in some (i.e. 1%)

$$\frac{MsY}{msy} \quad \frac{Sp}{Sp}$$

genotype plants which will pass examination since they have yellow endosperm. These plants will have to be rogued out in the field before their pollen is shed, but since these should be very few of them, the economics of doing so should be tolerable. The male fertility of the plants is readily apparent in the field before pollen is shed because of the readily identifiable tassels of plants male-sterile at the $ms_1$ locus.

The resulting homozygous male-sterile plants are then crossed with stock (3). All progeny plants will be heterozygous with equal proportions of the following stocks:

$$\frac{msy}{Ms(Rs) \, Y} \quad \frac{Sp}{-} \text{ and } \frac{msY}{Ms(Rs) \, Y} \quad \frac{Sp}{-}$$

All seed from this cross will be yellow and all plants from seeds of this stock will be phenotypically male-sterile. The presence of an active Spm copy including suppressor function in the plant genome will cause the dSpm functioning as a receptor factor to prevent expression of the male fertile allele in which it is inserted, resulting in male sterility. Seed maize of this stock can then be used in hybrid maize production by making a single cross with a male parent MsY plant of any other selected inbred line parental stock. All the F1 hybrid seed from this cross will be fully fertile in the farmers field.

EXAMPLE 1

Transposition of Spm Receptor Function to $ms_1$ Locus

A beginning stock line was obtained of maize seed mixed homozygous for the recessive male-sterile allele at the $ms_1$ locus and heterozygous for sterility at the same locus. The line was maintained by crossing heterozygous male-fertile plants to homozygous male-sterile plants.

The second beginning stock line used is referred to as bronze-mutable13. This line has been previously identified by one of the inventors here. Nelson & Klein, *Genetics*, 1984. This line has a receptor (Rs) of the Spm system located at the locus for bronze aleurone pigment (Bz). The resulting mutable bronze allele, designated bz-m13, conditions full pigment production in the absence of Spm but is suppressed and highly mutable when a full Spm copy is located elsewhere in the genome. The seeds of this line were heterozygous at the bz locus and had an active copy of Spm elsewhere in the genome as evidenced by variegated seed color. All seeds of this line were presumably homozygous for functional (male-fertile) alleles at all male-sterile loci, including $ms_1$. Plants grown from the kernels of this line were continually self-pollinated to maintain this line.

Both stocks were grown to maturity. By staggered planting, the plants of the two lines were synchronized to arrive at their sexual maturity at the same time. The pistillate flowers (silks) of the male-sterile plants were fertilized with pollen from the Spm; bronze-mutable13 line, i.e.

$$\frac{ms_1}{ms_1} \times \frac{Ms_1}{MS_1} \quad \frac{(Rs)}{(Rs)} \quad \frac{Spm}{Spm}$$

The F1 seeds resulting from this cross were grown to maturity in Florida during the winter of 1982-3, and in Wisconsin in spring 1983. When the plants began to flower, their tassels were scored for complete or partial pollen sterility visually or by staining pollen with acetocarmine. Without transposition, it would be expected that all F1 plants would be male fertile since they would be heterozygous at the male-sterile locus ($MS_1/ms_1$). However in the event of a transposition of an Spm receptor function (Rs) to a dominant allele at the $ms_1$ locus, the receptor would suppress the gene function in the presence of the Spm suppressor component, at the same locus or elsewhere in the genome. In some insertions, the Spm receptor function (Rs) may prevent gene expression by itself regardless of the presence or absence of Spm suppressor, which is not acceptable since gene expression in the absence of the Spm suppressor is desired.

Male-sterile plants in the F1 generation were identified from the crops in both Wisconsin and Florida. While some of these plants probably had a dSpm, or a copy of the entire Spm, at the $ms_1$ locus, there is also a certain level of spontaneous mutation and some non-genetic factors which can produce male sterility. In order to establish the transposition of the Rs to the male-sterile locus, the male-sterile plants were crossed by W64A, a popular inbred line. This cross brought the potentially controllable allele into a uniform known genetic background, and the progeny were then selfed and also testcrossed to homozygous male-sterile tester stocks ($ms_1/ms_1$; Spm/Spm). If the F1 plants were male-sterile due to spontaneous mutation, this selfing would produce 25% male-sterile plants since it would cross a heterozygous male-sterile/fertile with itself, and the testcross should produce 50% male-sterile plants since it would cross a heterozygous plant with a homozygous plant. If the F1 plants were male-sterile due to insertion of an Rs Spm function in the $ms_1$ locus, then the self and backcross progeny of some F1×W64A plants would be all fertile since some would lose the Spm suppressor thereby allowing expression of the gene. Plants from the F1×W64A cross which give rise to all fertile progeny have been identified. However, a similar result would also be observed if F1 plants which were male-sterile due to non-genetic factors or due to plants having an entire Spm copy at the $ms_1$ locus which could excise itself during growth of the plant if the Spm mutatot was still active. To screen those out, plants from the F1×W64A cross were selfed and testcrossed to a tester stock of homozygous male-sterile plants carrying the Spm suppressor. The progeny of this cross will be at least 50% fertile if the initial sterility was due to non-genetic factors, but should be about 50% or 100% male-sterile if the Rs is in the $ms_1$ locus depending on whether the plant testcrossed was homozygous or heterozygous for Rs function insertion in the $ms_1$ locus.

Example 2

A similar procedure has been followed as in Example 1 and is at a similar stage, except performed screening for the Rs at the $ms_2$ locus with tester stock of homozygous ($ms_2/ms_2$ Spm/Spm) male-sterile plants.

EXAMPLE 3

Identification of Spm elements which have lost mutator activity

Two seed stocks were used:

A. $\frac{bz-m13}{bz-m13}$ (no Spm); and

B. $\frac{bz}{bz} + \frac{Spm}{Spm}$

Kernels from the line A are uniformly reddish in the absence of the Spm suppressor function (i.e. another Spm copy). Kernels of the line B above are uniformly bronze. Plants from lines A and B were crossed during the summer of 1983 in Wisconsin using line A as a female parent. Ears from the progeny of that cross were examined for solid bronze kernels, it being expected in the absence of mutation that such kernels will have the bz-m13 mutated allele actively suppressed (which is why they are not red) but will have an inactive mutator as suggested by the lack of clones of colored cells. Kernels with a weak mutator, indicated by weak variegation (late-occurring and low frequency), were identified from these ears and the weak mutator has been confirmed by back-crossing them to stocks of line A as a female parent. These plants with a weak mutator component but still having the suppressor component of Spm, will now be back-crossed continually to stock from line A on a large scale to identify kernels in which Spm has lost the mutator activity completely, but retaining the Spm suppressor function. In this way it is possible to generate a maize line including the Spm suppressor function with an inactivated mutator function so that the Spm suppressor function is stable, and to then transfer the Spm suppressor function by itself to another line in the methods indicated below.

EXAMPLE 4

Transfer of Spm receptor (Rs) function at $ms_1$ locus to desired inbred lines

Once the insertion of the Rs receptor function (really a dSpm copy) into the desired male-sterile locus is firmly identified, it is then desirable to transfer that mutated male-fertile allele to the desired inbred line to be utilized for hybrid seed production. This method can be accomplished using the following stocks:
 A. Desired inbred line, for example, W64A.
 B. A line with the Spm receptor (Rs) function (a dSpm) inserted at $ms_1$ locus such that it does not condition sterility in the absence of the suppressor function of Spm, or complete Spm component in another portion of the genome. The lines created by Examples 1 or 2 above are suitable.
 C. A tester stock of plants homozygous male-sterile at the desired locus and carrying a complete Spm system (preferably without the mutator component) elsewhere in its genome. Since it does not matter if a receptor (Rs) function is located at another locus in the tester stock, we would utilize a doubly mutant line (ms/ms; bz-m13/bz-m13), in which the bz-m13 allele serves as an indication of the presence of Spm.

This procedure basically involves the crossing of the A stock, used as a recurrent parent, with the B stock utilized as a non-recurrent parent, and with the resulting progeny back-crossed to the recurrent parent for five or six generations. The progeny from the first back-cross, designated $BC_1$, and subsequent back-crosses, are then outcrossed to line C to select the plants carrying the male-sterile allele containing an Spm receptor function. In the final step the back-cross progeny are self-pollinated to obtain plants homozygous for the mutated allele. Testing for homozygous plants is done against the tester stock, since crosses of the homozygous allele having the receptor in it against the tester stock, line C above, would yield all male-sterile progeny while heterozygous ms/Ms plants crossed to the tester would product 50% male-fertile progeny.

EXAMPLE 5

Transfer of suppressor component to desired inbred line

Created in Example 3 above was an inbred stock having the stable Spm suppressor function, designated Sp. Again this may be a dSpm as long as suppressor activity is maintained, or a full Spm copy, although lack of mutator activity is preferred. In order to utilize the mutated male-sterile gene in hybrid plant production, it is now necessary to transfer this suppressor to the desired inbred line to be used in the procedure. This step requires the following stocks:
 A. The desired inbred line, for example, W64A.

B. $\frac{ms_1y}{ms_1y}$  $\frac{Sp}{Sp}$

C. A tester stock of the following:

$\frac{ms_1}{ms_1}$  $\frac{bz-m13}{bz-m13}$ (no Spm)

This process involves crossing the A and B stocks and then crossing the resulting progeny both to A as a recurrent parent and to line C as a test cross to pick out and select for the desired genotype. The process is repeated through five or six back-cross generations to obtain the genetic constitution of the desired inbred line of stock A. In the final step the progeny is selfed and the desired stocks are selected by crossing the selfed progeny to the tester stock to test for the presence of the suppressor component.

EXAMPLE 6

Male sterile seed production

Male sterile seed production will require the following three stocks all of which are transferred into the desired background line which will be the female parent in hybrid maize production.

$$A. \frac{ms_1y}{ms_1y} \quad \frac{Sp}{Sp}$$

$$B. \frac{Ms_1y}{ms_1Y} \quad \frac{Sp}{Sp}$$

$$C. \frac{Ms_1(Rs) \; Y}{Ms_1(Rs) \; Y}$$

The production of male-sterile seed would begin by crossing lines A and B with line A being the female parent. The result of this cross, ignoring recombinations, will be 50% each of the following two genotypes $$\frac{ms_1y}{ms_1Y} \quad \frac{Sp}{Sp} \quad \frac{Ms_1y}{ms_1y} \quad \frac{Sp}{Sp}$$

which are respectively male-sterile with yellow endosperm and male fertile with white endosperm.

There may also be some recombinations involved which could give rise to homozygous male-sterile with homozygous white kernels or to heterozygous male fertile with heterozygous yellow kernels. In any event, it will be noted that generally the plants heterozygous for male sterility, or the male fertile kernels from the above cross, will be white while the male-sterile kernels will be yellow. Accordingly, an optical screen for the kernels can be determined to leave largely only the homozygous male-sterile kernels as selected by color. Accordingly, by an optical screening of the results of this cross, the male-sterile seed can be selected. Recombination may result in some male fertile yellow genotypes, but these will be in any event less than 1% of the total number of plants and will be able to be rogued out easily in the field before their pollen is shed, which can be easily done in the field because of difference in tassel appearance.

EXAMPLE 8

Hybrid seed production - increased plot for male-sterile seed

In order to take the results from Example 7 above and increase the quantity of the male-sterile seed sufficient for large scale seed production the following procedure will be adopted, again using the same three original stocks as mentioned in Example 7 above. The plants from line A of Example 7 will be crossed with plants of line C of Example 7 with the line A being used as the female parent. That cross will give equal proportions of the following two stocks:

$$\frac{ms_1y}{Ms_1(Rs) \; Y} \quad \frac{Sp}{-} \quad \frac{ms_1Y}{Ms_1(Rs) \; Y} \quad \frac{Sp}{-}$$

As can be seen, both of these stocks will be male-sterile because the Spm suppressor function will activate the receptor function located in the mutant male fertile allele to prevent expression of the male fertile allele. All the kernels will be yellow. Therefore all of the kernels from this generation can be collected and will give rise to male-sterile plants.

EXAMPLE 9

Hybrid seed production

All of the seed will be collected as generated in Example 8 above and will be planted. All of the plants will be male-sterile and can be used as a female parent in making a cross with any selected male parent inbred line. The seed produced by the female parent will be the F1 hybrid seed which can be sold to farmers and all plants will be both male and female fertile assuming that the male parent to the hybrid generation is homozygous male fertile. As a consequence of the use of the y allele as a marker, approximately 1/64 of the production in the farmer's field would be expected to have white kernels. This should not prove objectionable.

As can be seen from the above examples, this method can be carried out with any existing inbred line of maize, and while significant manipulations are involved in transferring and creating the appropriate stocks in the inbred line, all of these manipulations would involve only one of the two potential parents of the desired hybrid, i.e. the female parent, and no particular alterations are at all required to the male donor parent of the hybrid maize generation.

Maize seed of line bronze-mutatable13 has been deposited at the American Type Culture Collection, Rockville, MD., USA (ATCC) and are thus made available. Availability of these seeds is not to be construed as a license to practice this invention in contravention of the rights granted under the authority of any government in accordance with its patent laws.

The ATCC accession number for this deposit is 40189.

We claim:

1. A method of producing genic male-sterile maize seed comprising the steps of:
   pollinating first maize plants homozygous for male sterility at a selected male-sterile locus and also homozygous for a suppression factor at another locus in its genome with pollen from second maize plants homozygous for an insertion mutated male-fertile allele allelic with the male-sterile locus and mutated by the insertion therein of a transposition receptor factor whose relation to the male-fertile allele is such as to allow male-fertility in the absence of the suppression factor and to prevent male fertility in the presence of the suppression factor; and
   harvesting the seed produced on the homozygous male-sterile plants.

2. A method as claimed in claim 1 wherein the suppression factor and the receptor factor functional elements are elements or complete copies of the Spm transposable element system.

3. A method as claimed in claim 2 wherein the mutator of the Spm is attenuated or inactivated.

4. A method as claimed in claim 3 wherein the male-sterile locus ms-$_1$ is used and the allele for male sterility is linked with a dominant allele for yellow endosperm color so that endosperm color can be used to screen for male-sterile seed from a cross of homozygous male-sterile plants to heterozygous male fertile ones.

5. Male-sterile seed maize produced by the method of claim 2.

6. Maize seed produced by the method of claim 5.

7. A method as claimed in claim 1 wherein the male-sterile locus is selected from the group consisting of the male-sterile $ms_1$ and $ms_2$ loci.

8. Male-sterile seed maize produced by the method of claim 4.

9. Maize seed produced by the method of claim 8.

10. Male-sterile seed maize produced by the method of any of claim 1.

11. A method of producing hybrid maize using a genic male-sterile parent comprising the steps of:
   breeding a first maize line homozygous at a selected male-sterile locus and carrying a suppression factor in its genome;
   breeding a second maize line homozygous for an insertion mutated male-fertile allele allelic with the male-sterile locus and mutated by the insertion therein of a receptor factor which is positioned relative to the male-fertile allele so as to allow the male-fertile allele to condition male fertility in the absence of the suppression factor and to prevent expression of male fertility in the presence of the suppression factor;
   pollinating plants of the first line with pollen from the plants of the second line and harvesting the seed produced in the plants of the first line;
   cultivating said seed to produce male-sterile mature maize plants;
   pollinating said male-sterile plants with pollen from male fertile plants of a selected third maize line; and
   harvesting the seed produced in the male-sterile plants.

12. A method as claimed in claim 11 wherein the suppression factor and the receptor factor functional elements are elements defective copies, or entire copies of the Spm transposable element system.

13. A method as claimed in claim 12 wherein the mutator of the Spm is attenuated or inactivated.

14. A method as claimed in claim 13 wherein the male-sterile locus $ms_1$ is used and the allele for male-sterility is linked with the dominant allele for yellow endosperm color so that endosperm color can be used to screen for male-sterile seed from a cross of homozygous male-sterile plants to heterozygous male-fertile ones, and further including after said first pollinating step and before said cultivating step of screening for yellow endosperm color associated with male-sterile seed.

15. Maize seed produced by the method of claim 12.

16. A method as claimed in claim 11 wherein the male-sterile locus is selected from the group consisting of the $ms_1$ and $ms_2$ loci.

17. A method as claimed in claim 11 wherein the first and second maize lines are created from the same background inbred maize line.

18. Maize seed which upon cultivation will yield genetically stable male-sterile maize plants, comprising, in its genome:
   a suppression factor capable of actuation of a receptor factor elsewhere in the genome;
   a male-sterile allele; and
   an insertion mutated male fertile allele allelic with the male-sterile allele and mutated by the insertion therein of a receptor factor located relative to the male-fertile allele so as to prevent expression of male fertility in the presence of the suppression factor and to allow male fertility in the absence of the suppression factor.

19. Maize seed as claimed in claim 18 wherein the suppression factor and the receptor factor are elements, defective copies, or full copies of the Spm transposable element system.

20. Maize seed as claimed in claim 19 wherein the mutator of the Spm system has been attenuated or inactivated.

* * * * *